United States Patent [19]

Fukuda

[11] Patent Number: 4,760,838

[45] Date of Patent: Aug. 2, 1988

[54] ENDOSCOPE APPARATUS AND AIR-/LIQUID-SUPPLY DEVICE THEREFOR

[75] Inventor: Hiroyuki Fukuda, Tokyo, Japan

[73] Assignee: Olympus Optical Co., Ltd., Tokyo, Japan

[21] Appl. No.: 56,998

[22] Filed: Jun. 2, 1987

[30] Foreign Application Priority Data

Jun. 12, 1986 [JP] Japan ............................ 61-89552[U]

[51] Int. Cl.$^4$ ................................................ A61B 1/12
[52] U.S. Cl. ..................................................... 128/4
[58] Field of Search ............................ 128/3, 4, 5, 6, 7

[56] References Cited

U.S. PATENT DOCUMENTS

| 4,261,343 | 4/1981 | Ouchi et al. | 128/4 |
| 4,325,362 | 4/1982 | Ouchi et al. | 128/4 |
| 4,402,310 | 9/1983 | Kimura | 128/4 |
| 4,552,130 | 11/1985 | Kinoshita | 128/4 |

FOREIGN PATENT DOCUMENTS 59-64104  4/1984  Japan .

Primary Examiner—William H. Grieb
Attorney, Agent, or Firm—Ladas & Parry

[57] ABSTRACT

An endoscope apparatus includes an endoscope body and an air-/liquid-supply device connected thereto. Provided at the distal end of an insertion section of the body are an observation window and a nozzle directed toward the window. Air and liquid supply pipes extend from the nozzle, through the endoscope body. The supply device has a tank for storing water therein. The inside space of the tank is divided by a partition plate into a first chamber on the water side and a second chamber. Compressed air supplied from a first pump to the inside space is supplied to the air supply pipe through a first supply pipe, and compresses the water in the tank, thereby supplying the water to the liquid supply pipe through a second pipe. Air having a pressure higher than that of the first pump is supplied from a second pump to the second chamber. The high-pressure air is prevented from flowing into the first chamber, and is immediately supplied to the air supply pipe.

7 Claims, 2 Drawing Sheets

ENDOSCOPE APPARATUS AND AIR-/LIQUID-SUPPLY DEVICE THEREFOR

BACKGROUND OF THE INVENTION

The present invention relates to an endoscope apparatus and, more particularly, to an endoscope apparatus comprising an air-/liquid-supply device.

When a body cavity is examined, using an endoscope, an insertion section of the endoscope is inserted into the body cavity. Upon insertion, filth, mucus, and the like tend to become attached to an observation window incorporated in the insertion section. In this case, a portion of interest cannot be properly observed. Therefore, the observation window is usually cleaned by using an air-/liquid-supply device, thereby removing the filth, mucus, and the like attached to it.

In general, an endoscope comprises a spray nozzle arranged on the insertion section and directed toward an observation window, and air- and liquid-supply pipes communicating with this nozzle. The air-/liquid-supply device comprises a liquid storage tank, connected to the air- and liquid-supply pipes, for storing a liquid, and an air pump connected to the tank. When the observation window is to be cleaned, the liquid in the liquid storage tank is compressed by way of the air pump, is fed into the liquid-supply pipe, and sprayed out of the nozzle, onto the observation window, to thereby remove filth attached thereto. After this, the compressed air from the air pump is blown out of the nozzle, through the air-supply pipe, so as to remove the liquid clinging to the observation window.

However, following the above cleaning process, waterdrops sometimes remain on the observation window. When this occurs, it is difficult to perform a proper diagnosis and carry out the appropriate medical treatment, because the field of observation is partially obscured by the waterdrops. Thus, when a region of interest is to be treated by using the RF treatment device, a laser treatment device, or the like, a region other than the actual region of interest may be erroneously damaged.

Therefore, techniques have been proposed for reliably removing waterdrops remaining on the observation window, by means of blowing high-pressure air from the nozzle. For example, an apparatus having a high-pressure air supply means connected to an intermediate portion of an air-supply pipe of an endoscope or to a liquid storage tank is disclosed in Japanese Utility Model Disclosure (Kokai) No. 59-64101.

However, when the air-supply means is arranged in the operation section of an endoscope, and connected to the air-supply pipe, the weight of the operation section increases considerably, thus degrading the operability of the endoscope. When the air-supply means is connected to an air tank, there is a significant time delay before high-pressure air is blown from the nozzle, after the air-supply means has been activated.

SUMMARY OF THE INVENTION

The present invention has been developed in consideration of the above situation, and has its object to provide an endoscope apparatus and an air-/liquid-supply device therefor, wherein waterdrops clinging to an observation window can be properly removed by using high-pressure air, and good operability and response are assured.

In order to achieve the above object, an endoscope apparatus of the present invention comprises: an endoscope body including an operation section, an insertion section extending therefrom, an observation window provided at a distal end portion of the insertion section, a spray nozzle arranged on the distal end portion of the insertion section and directed toward the observation window, an air-supply pipe connected to the nozzle and extending through the operation section and the insertion section, and a liquid-supply pipe connected to the nozzle and extending through the operation section and the insertion section; and an air-/liquid-supply device for supplying air and a liquid to the air- and liquid-supply pipes, respectively, the device including a liquid storage tank for storing the liquid, a partition member, arranged inside the tank, for partitioning a space, defined by the surface of the liquid and the inner wall surface of the tank, into a first chamber on the liquid side and a second chamber, the partition member having communicating means for causing the first chamber to communicate with the second chamber, a first supply pipe, one end of which is connected to the air-supply pipe, and the other end of which communicates with the second chamber, a second supply pipe, one end of which is connected to the liquid-supply pipe, and the other end of which is dipped in the liquid stored inside the tank, a first air-supply means for supplying compressed air to the space and to the first supply pipe, and supplying the liquid stored inside the tank to the second supply pipe, a second air-supply means for supplying air having a pressure higher than that of the first air-supply means, to the second chamber, and supplying compressed air to the first supply pipe, and a regulating means for preventing the compressed air supplied from the second air-supply means to the second chamber from flowing into the first chamber.

DETAILED DESCRIPTION OF THE PREFFERED EMBODIMENTS

Embodiments of the present invention will now be described, with reference to the accompanying drawings.

Figure 1:
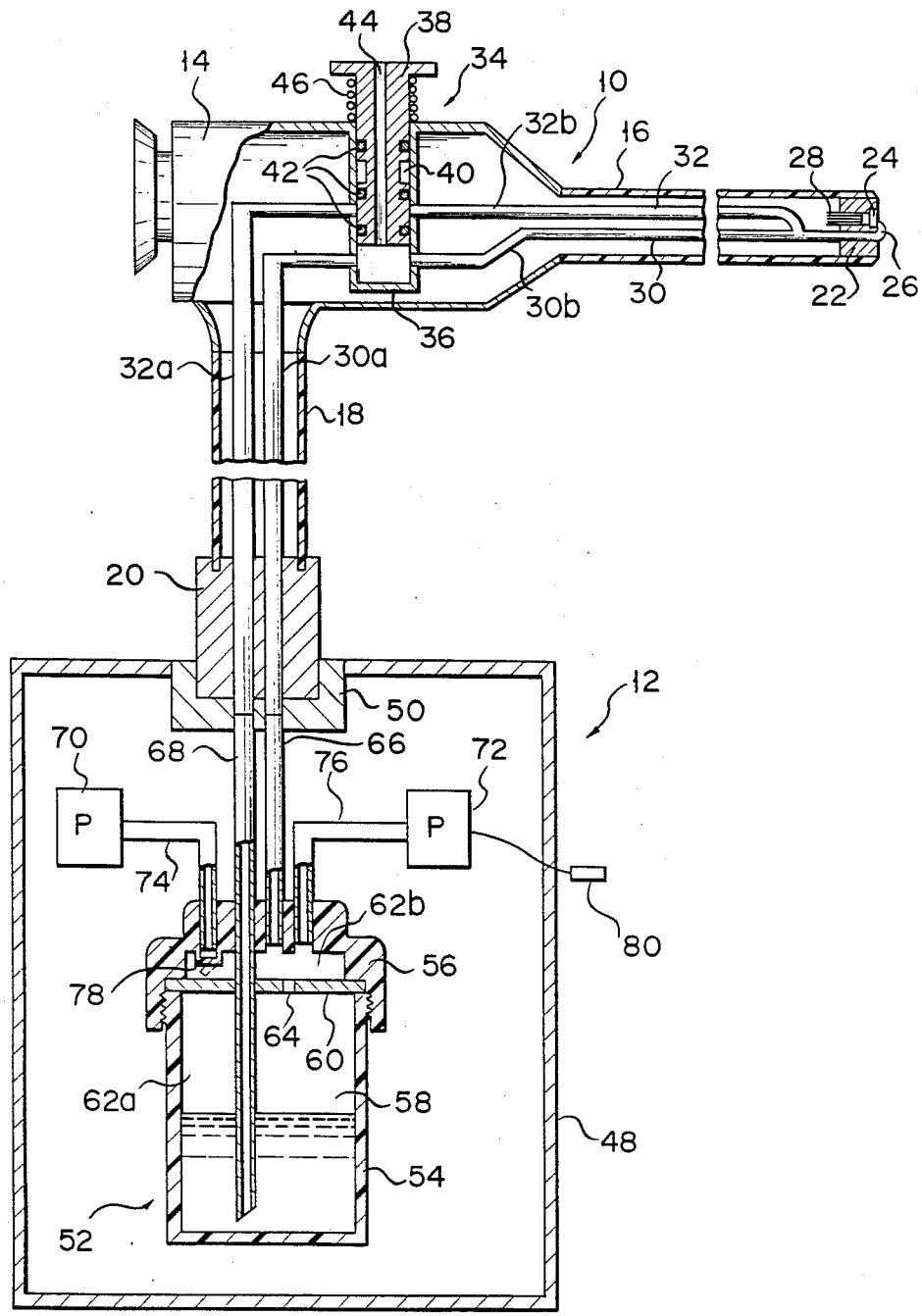
FIG. 1 is a sectional view of an endoscope apparatus according to an embodiment of the present invention.

FIG. 1 shows the overall endoscope apparatus of the present invention. The endoscope apparatus comprises endoscope body 10 and air-/liquid-supply device 12 connected to endoscope body 10.

Endoscope body 10 comprises operation section 14, insertion section 16 extending therefrom to be inserted into an body cavity, and universal cord 18 extending from operation section 14. Connector 20 is attached to the extended end of universal cord 18. Hard distal end member 22 is mounted on the extended end of insertion section 16. Observation window 24 and spray nozzle 26 directed thereto are mounted on the distal end face of end member 22. Image guide 28 formed of optical fibers is fixed at its distal end to observation window 24, and extends to operation section 14 through insertion section 16. One end of air-supply pipe 30 is connected to nozzle 26. Pipe 30 extends from nozzle 26 to connector 20 through insertion section 16, operation section 14, and universal cord 18. The other end of pipe 30 projects outward from connector 20. Liquid-supply pipe 32 extends through endoscope body 10 in parallel with air-supply pipe 30. One end of pipe 32 is connected to air-supply pipe 30 near nozzle 26, and the other end thereof projects outward from connector 20.

Operation switch 34 for switching communicating conditions of air- and liquid-supply pipes 30 and 32 is arranged in operation section 14. Operation switch 34 has cylinder 36 arranged in operation section 14. One end of cylinder 36 is open at the outer face of operation section 14. Cylinder 36 is connected to intermediate portions of the air- and liquid-supply pipes. More specifically, the ends of upstream portion 30a and downstream portion 30b of air-supply pipe 30 are connected to a lower peripheral wall portion of cylinder 36, and the ends of upstream portion 32a and downstream portion 32b of liquid-supply pipe 32 are connected to an intermediate peripheral wall portion of cylinder 36.

Piston 38 is inserted into cylinder 36, and one end of piston 38 extends outward therefrom. On the outer periphery of piston 38, annular groove 40 is formed at an intermediate portion thereof in its axial direction and O-rings 42 are fitted in both sides of the groove. Through hole 44 is formed in piston 38 to extend along the axial direction thereof. Piston 38 is biased to a first position shown in FIG. 1 by compression coil spring 46 arranged therearound. Upstream portion 30a and downstream portion 30b of air-supply pipe 30 communicate with each other through a space inside cylinder 36 while piston 38 is positioned at the first position. On the contrary, in this state, upstream portion 32a and downstream portion 32b of liquid pipe 32 are disconnected from each other by piston 38. When piston 38 is pushed into cylinder 36 against the biasing force of spring 46 and groove 40 is shifted to a position facing the ends of upstream portion 32a and downstream portion 32b of liquid-supply pipe 32, i.e. when the piston is moved to a second position, groove 40 causes upstream portion 32a to communicate with downstream portion 32b. In this state, air-supply pipe 30 is closed by piston 38.

Air-/liquid-supply device 12 comprises housing 48. Socket 50 is arranged on an upper wall of housing 48, and connector 20 of endoscope body 10 is connected to socket 50. Liquid tank 52 is located in housing 48. Liquid tank 52 includes cylindrical tank body 54 with a bottom for storing water and cap 56 air-tightly and detachably fitted on an opening edge thereof. Space 58, which is defined by the inner surfaces of cap 56 and tank body 54, and the surface of the water, is divided by partition plate 60 arranged inside the space into first chamber 62a on the water surface side and second chamber 62b on the cap 56 side. Partition plate 60 is held in tank body 54 while clamped by the opening edge thereof and cap 56. Second chamber 62b is formed sufficiently smaller than first chamber 62a. Communicating hole 64 is formed in partition plate 60 to cause first chamber 62a to communicate with second chamber 62b. Communicating hole 64 has a flow resistance higher than that of air-supply pipe 30 of the endoscope body.

Air- and liquid-supply pipes 30 and 32 of endoscope body 10 are connected to tank 52 through first and second supply pipes 66 and 68 when connector 20 is connected to socket 50. One end of supply pipe 66 is fixed in socket 50 and connected to the end of air-supply pipe 30. The other end of pipe 66 is fixed to cap 56 and open to second chamber 62b. One end of pipe 68 is fixed in socket 50 and connected to liquid-supply pipe 32, and the other end of pipe 68 extends near the bottom of tank body 54 through cap 56 and partition plate 60, and is dipped in water inside the tank.

First and second air-supply pumps 70 and 72 are arranged inside housing 48. Pumps 70 and 72 communicate with second chamber 62b through pipes 74 and 76, respectively. An output power of second pump 72 is higher than that of first pump 70, thereby supplying air at a higher pressure. Check valve 78 is provided at the end of pipe 74 so as to prevent the air from reversely flowing from second chamber 62b to pump 70. In FIG. 1, reference numeral 80 denotes a switch for operating second pump 72. This switch may be arranged either on operation portion 14 of the endoscope body or outside air-/liquid-supply device 12 as a foot switch.

The operation of the endoscope apparatus with the above arrangement will be described.

When observation window 24 is to be cleaned while insertion section 16 of endoscope body 10 is inserted into a body cavity, first pump 70 is driven in the first place. In this case, piston 38 of operation switch 34 is positioned at the first position. Air of a relatively slow speed and a low pressure from pump 70 is flowed into second chamber 62b of tank 52 through pipe 74. Since communicating hole 64 has a high flow resistance, little of the air flowing into chamber 62 passes through communicating hole 64, but most of it is discharged to the atmosphere after passing through first supply pipe 66, upstream portion 30a of air-supply pipe 30, cylinder 36, and through hole 44 of piston 38.

In this state, piston 38 is pushed into the second position while through hole 44 is closed by a finger. Thus, air-supply pipe 30 is closed by piston 38, while liquid-supply pipe 32 is brought into a communicating state. As a result, the air flowing into second chamber 62a cannot flow into air-supply pipe 30, but flows into first chamber 62a through communicating hole 64, thereby compressing the water. Compressed water inside tank 54 is introduced to nozzle 26 through second supply pipe 68 and liquid-supply pipe 32, and sprayed on observation window 24 from nozzle 26, thereby washing off filth, mucus, and the like attached to observation window 24.

Thereafter, piston 38 is moved back to the first position while through hole 44 is closed by the finger. Thus, air-supply pipe 30 is brought into a communicating state so that the air supplied from pump 70 is introduced to nozzle 26 through the air-supply pipe, and blown against observation window 24 from nozzle 26, thereby blowing off waterdrops attached to the observation window.

Waterdrops are sometimes left on the surface of observation window 24 even after performing the above cleaning operation. In such a case, switch 80 is turned on so as to operate second pump 72 while through hole 44 of piston 38 is closed by the finger. Thus, high-pressure air is rapidly supplied to second chamber 62b from pump 72. Since communicating hole 64 of tank 54 has a flow resistance higher than that of air-supply pipe 30, little of the high-pressure air supplied to second chamber 62b passes through the communicating hole, but most of it flows into air-supply pipe 30. As a result, the high-pressure air is blown against observation window 24 from nozzle 26, thereby reliably removing the waterdrops left on the observation window.

According to the endoscope apparatus with the above arrangement, waterdrops left on the observation window can be securely removed by high-pressure air. Therefore, a correct diagnosis and a treatment can be made. In addition, since the high-pressure air from pump 72 is supplied to chamber 62 of a small volume, and communicating hole 64 is formed such that its flow resistance is higher that of air-supply pipe of endoscope body 10, the high-pressure air supplied to chamber 62b does not flow into first chamber 62a. For this reason, a high pressure is instantaneously developed inside second chamber 62b, so that high-pressure air can be immediately blown from nozzle 26 via air-supply pipe 30.

Since the high-pressure air supplied from pump 72 does not flow into first chamber 62a, high-pressure air can be blown from nozzle 26 in a predetermined condition regardless of the amount of water in tank 54. In other words, the volume of the first chamber varies in accordance with the amount of the water inside tank 52, so that if high-pressure air from pump 72 is supplied to both first and second chambers 62a and 62b, a time required to sufficiently increase a pressure inside the first and second chambers varies depending on the amount of water. According to the present invention, such a problem can be eliminated.

Furthermore, since pump 72 is arranged separately from endoscope body 10, the endoscope body is neither bulky nor heavy.

As has been described above, there can be provided an endoscope apparatus which can reliably remove waterdrops from the observation window, and which has good operability and response.

The present invention is not limited to the above embodiment, and various changes and modifications may be made within the spirit and scope of the invention.

Figure 2:
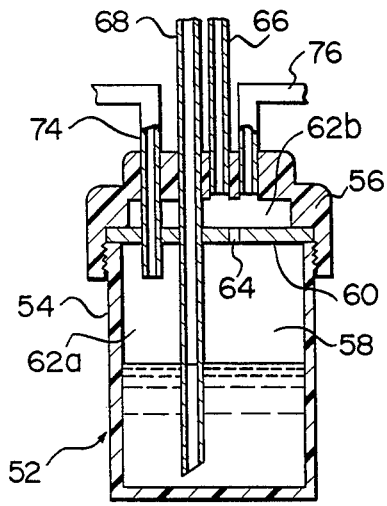
FIGS. 2 to 5 respectively are sectional views showing main parts of air-/liquid-supply devices according to second to fifth embodiments of the present invention.

For example, as is shown in FIG. 2, the end portion of pipe 74 connected to first pump 70 may extend into first chamber 62a through partition plate 60.

Figure 3:
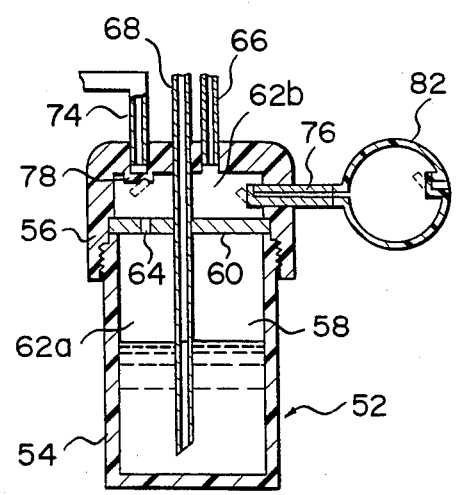

As is shown in FIG. 3, manual pump 82 may be used in place of second air pump 72 as a high-pressure air supply means. Manual pump 82 is constituted by a hollow rubber ball and connected to pipe 76. Since manual pump 82 is capable of only supplying a small amount of air, if the volume of space 58 inside tank 52 is large, it is difficult to supply high-pressure air to the nozzle. However, since the volume of second chamber 62b communicating with pump 82 is set to be small, high-pressure air can be reliably blown from the nozzle even by using the manual pump.

Figure 4:
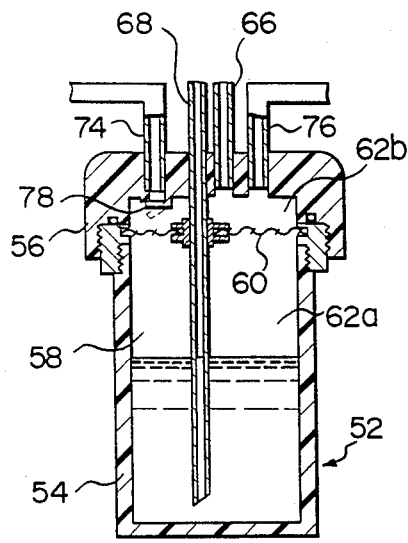

As is shown in FIG. 4, a cloth having air permeability may be used in place of partition plate 60. In this case, however, the cloth is required to have a flow resistance higher than that of the air-supply pipe of the endoscope body.

Note that any material other than the cloth, e.g., a synthetic resin film or a wire net, may be employed as long as it satisfies the above condition of flow resistance.

Figure 5:
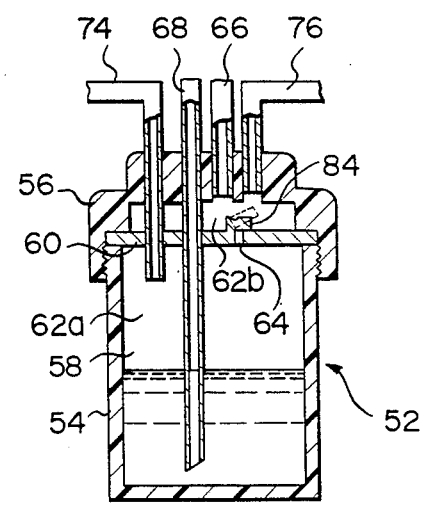

According to a fifth embodiment shown in FIG. 5, the end portion of pipe 74 connected to first pump 70 extends into first chamber 62a through cap 56 and partition 60 of tank 52. Check valve 84 is provided on partition plate 60 so as to oppose the upper end opening of communicating hole 64. Check valve 84 prevents air inside second chamber 62b from flowing into first chamber 62a via communicating hole 64. Note that in the fifth embodiment, communicating hole 64 is not required to have a flow resistance higher than that of air-supply pipe 30 of endoscope body 10.

In the second to fifth embodiments with the above arrangements, advantages equivalent to that in the first embodiment can be obtained. In FIGS. 2 to 5, the same reference numerals as in the first embodiment denote the same parts as in FIG. 1, and a detailed description thereof has been omitted.

What is claimed is:

1. An endoscope apparatus comprising: an endoscope body including
   an operation section,
   an insertion section extending from the operation section,
   an observation window arranged at a distal end portion of the insertion section,
   a spray nozzle provided at the distal end portion of the insertion section and directed toward the observation window,
   an air-supply pipe extending through the operation section and insertion section, and connected to the nozzle, and
   a liquid-supply pipe extending through the operation section and insertion section, and connected to the nozzle; and
   an air-/liquid-supply device for supplying air and a liquid to said air- and liquid-supply pipes, respectively, the air-/liquid-supply device including
   a liquid storage tank for storing a liquid,
   a partition member arranged in the tank, to divide a space defined by the surface of the liquid and the inner surface of the tank into a first chamber on the liquid side and a second chamber, the partition member having communicating means for enabling the first chamber to communicate with the second chamber,
   a first supply pipe having one end connected to the air-supply pipe and the other end communicating with the second chamber,
   a second supply pipe having one end connected to the liquid-supply pipe and the other end dipped in the liquid stored in the tank,
   first air-supply means, for supplying compressed air to the space, so as to supply the compressed air to the first supply pipe and to supply the liquid stored in the tank to the second supply pipe,
   second air-supply means, for supplying air having a pressure higher than that of the first air-supply means, to the second chamber, and further, to the first supply pipe, and
   regulating means for preventing compressed air supplied from the second air-supply means to said second chamber from flowing into the first chamber.

2. An apparatus according to claim 1, wherein a volume of said second chamber is smaller than that of the first chamber.

3. An apparatus according to claim 1, wherein said communicating means includes a communication hole which is formed to extend through the partition member, and which has a flow resistance higher than that of the air-supply pipe, and constitutes the regulating means.

4. An apparatus according to claim 1, wherein said partition member is formed of a material having air permeability and a flow resistance higher than that of the air-supply pipe.

5. An apparatus according to claim 1, wherein said communicating means includes a communication hole formed to extend through the partition member, and said regulating means includes a check valve provided at the partition member, so as to open/close the communication hole.

6. An apparatus according to claim 1, wherein said endoscope body includes an operation switch, arranged at the operation section, for opening and closing the air- and liquid-supply pipes, the switch having a switching member which is arranged to be shiftable to a first position, for enabling the air-supply pipe to be in a communicating state, while closing the liquid-supply pipe, and to a second position, for enabling the liquid-supply pipe to be in a communicating state, while closing the air-supply pipe.

7. An air-/liquid-supply device for supplying compressed air and a liquid to air- and liquid-supply pipes, respectively, the supply pipes being connected to a nozzle provided at a distal end portion of an insertion section of an endoscope, and directed to an observation window of the endoscope, comprising:
- a tank for storing a liquid;
- a partition member arranged in the tank, to divide a space defined by the surface of the liquid and the inner surface of the tank into a first chamber on the liquid side and a second chamber, the partition member having communicating means for enabling the first chamber to communicate with the second chamber;
- a first supply pipe having one end connected to the air-supply pipe, and the other end communicating with the second chamber;
- a second supply pipe having one end connected to the liquid-supply pipe, and the other end dipped in the liquid stored in the tank;
- first air-supply means, for supplying compressed air to the space, so as to supply the compressed air to the first supply pipe and to supply the liquid stored in the tank to the second supply pipe;
- second air-supply means, for supplying air, having a pressure higher than that of the first air-supply means, to the second chamber, and further, to the first supply pipe; and
- regulating means for preventing compressed air supplied from the second air-supply means to the second chamber from flowing into the first chamber.

* * * * *